United States Patent
Beer et al.

(10) Patent No.: US 12,127,866 B2
(45) Date of Patent: Oct. 29, 2024

(54) MEDICAL DEVICE AND METHOD FOR OPERATING A MEDICAL DEVICE

(71) Applicant: Siemens Healthcare GmbH, Erlangen (DE)

(72) Inventors: Alexander Beer, Kulmbach (DE); Andreas Deinlein, Bayreuth (DE); Thomas Dippl, Pressath (DE); Franz Dirauf, Bad Staffelstein (DE); Matthias Mueller, Bamberg (DE); Claus-Guenter Schliermann, Kemnath (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 982 days.

(21) Appl. No.: 17/046,025

(22) PCT Filed: Mar. 7, 2019

(86) PCT No.: PCT/EP2019/055652
§ 371 (c)(1),
(2) Date: Oct. 8, 2020

(87) PCT Pub. No.: WO2019/201506
PCT Pub. Date: Oct. 24, 2019

(65) Prior Publication Data
US 2021/0038174 A1 Feb. 11, 2021

(30) Foreign Application Priority Data
Apr. 16, 2018 (DE) .................... 10 2018 205 758.3

(51) Int. Cl.
*A61B 6/04* (2006.01)
*A61B 6/00* (2006.01)
*A61B 6/10* (2006.01)

(52) U.S. Cl.
CPC ............ *A61B 6/0487* (2020.08); *A61B 6/102* (2013.01); *A61B 6/4464* (2013.01)

(58) Field of Classification Search
CPC ....... A61B 6/0487; A61B 6/102; A61B 6/547; A61G 2203/726; A61G 7/018
See application file for complete search history.

(56) References Cited

U.S. PATENT DOCUMENTS 6,814,490 B1  11/2004  Suhm et al.
9,228,885 B2   1/2016  Zerhusen et al.
(Continued)

FOREIGN PATENT DOCUMENTS

CN   1486673 A    4/2004
CN  101034071 A    9/2007
(Continued)

OTHER PUBLICATIONS

"Robots and robotic devices—Collaborative robots"; ISO/TS 15066; First Edition Feb. 15, 2016.
(Continued)

*Primary Examiner* — Fredrick C Conley
(74) *Attorney, Agent, or Firm* — Harness, Dickey & Pierce, P.L.C.

(57) ABSTRACT

A medical device of an embodiment includes at least one movably mounted and motor-adjustable component; at least one drive unit for adjusting the at least one component; at least one motor control unit associated with the drive unit; and at least one sensing unit for sensing a position parameter dependent on the position of the at least one component. According to an embodiment of the invention, a safety function is integrated in the motor control unit. The safety function limits at least one operating parameter associated with the motion of the at least one component to be performed. An apparatus control unit controls the drive unit (Continued)

in dependence on the position parameter in accordance with the safety function. At least one embodiment of the invention further relates to a method for operating a medical device.

20 Claims, 1 Drawing Sheet

(56) References Cited

U.S. PATENT DOCUMENTS

| | | | |
|---|---|---|---|
| 9,668,768 B2 | 6/2017 | Piron et al. | |
| 2004/0042587 A1 | 3/2004 | Deshpande | |
| 2008/0034248 A1 | 2/2008 | Danzer et al. | |
| 2008/0162046 A1* | 7/2008 | Kotian | A61B 6/566 |
| | | | 701/300 |
| 2008/0258929 A1* | 10/2008 | Maschke | A61B 6/547 |
| | | | 340/686.1 |
| 2010/0061509 A1 | 3/2010 | D'Ambrosio et al. | |
| 2011/0087416 A1 | 4/2011 | Patmore | |
| 2016/0199141 A1 | 7/2016 | Mewes et al. | |
| 2016/0296297 A1 | 10/2016 | Perplies et al. | |
| 2016/0367415 A1* | 12/2016 | Hayes | A61G 1/0275 |
| 2017/0303882 A1* | 10/2017 | Ficarra | A61B 6/44 |
| 2018/0049832 A1 | 2/2018 | Eckert et al. | |
| 2019/0209104 A1* | 7/2019 | Dirauf | G05D 1/0255 |
| 2020/0146639 A1 | 5/2020 | Bentolila et al. | |
| 2021/0219927 A1* | 7/2021 | Dencovski | A61B 90/35 |
| 2022/0096027 A1* | 3/2022 | Deinlein | A61B 6/547 |

FOREIGN PATENT DOCUMENTS

| | | |
|---|---|---|
| CN | 101061960 A | 10/2007 |
| CN | 104983438 A | 10/2015 |
| CN | 105007821 A | 10/2015 |
| CN | 105708461 A | 6/2016 |
| DE | 102004040059 A1 | 2/2006 |
| DE | 102012205549 A1 | 10/2013 |
| DE | 102016204618 A1 | 9/2017 |
| EP | 1246566 B1 | 12/2004 |
| WO | WO 2015070947 A1 | 5/2015 |

OTHER PUBLICATIONS

International Search Report PCT/ISA/210 for International Application No. PCT/EP2019/055652 dated Jun. 25, 2019.
Written Opinion of the International Searching Authority PCT/ISA/237 for International Application No. PCT/EP2019/055652 dated Jun. 25, 2019.
"Sinumerik 840D sl Safety Integrated plus"; Prior Art Publishing, Dieffenbachstrasse 33 , D-10967 Berlin, Germany; Mar. 29, 2018 (Mar. 29, 2018), XP040694361.

* cited by examiner

MEDICAL DEVICE AND METHOD FOR OPERATING A MEDICAL DEVICE

PRIORITY STATEMENT

This application is the national phase under 35 U.S.C. § 371 of PCT International Application No. PCT/EP2019/055652 which has an International filing date of Mar. 7, 2019, which designated the United States of America and which claims priority to German application no. 10 2018 205 758.3 filed Apr. 16, 2018, the entire contents of each of which are hereby incorporated by reference herein, in their entirety and for all purposes.

FIELD

An embodiment of the disclosure generally relates to a medical device comprising at least one movably mounted and motor-adjustable component, at least one drive unit for adjusting the at least one component, at least one motor control unit associated with the drive unit and at least one sensing unit for sensing a location parameter dependent on the position of the at least one component. An embodiment of the disclosure further generally relates to a method for operating a medical device of this type.

BACKGROUND

Medical or medical-technical devices in particular for diagnostics and/or intervention typically require a movement of mechanical axes, in order, for instance, to suitably position a patient relative to imaging or therapy-relevant components, such as, for instance, an x-ray emitter or detector. With simple embodiments, the medical device is positioned manually by way of corresponding user effort. With superior embodiments, these movements are generally carried out in a motor-driven manner. Motor-driven movements are generally fraught with risk. This requires the realization of safety concepts in order to avoid personal injuries.

SUMMARY

The inventors have discovered that in conventional safety concepts, the user must constantly monitor the device movement and stop the same without delay in the event of imminent danger. This is frequently achieved by a motor-driven movement of the motor-adjustable component only then being enabled if the user permanently actuates a release button (also: dead man grip, dead man switch). If the release is no longer actuated, the movement is stopped automatically. The responsibility to avoid risks lies accordingly with the user.

At least one embodiment of the present invention improves the protection against injury of medical devices with motor-adjustable components.

Embodiments are directed to a medical device and a method for operating a medical device.

Advantageous embodiments of the invention are the subject matter of the claims.

A medical device comprises
at least one movably mounted and motor-adjustable component,
at least one drive unit for adjusting the at least one component,
at least one motor control unit associated with the drive unit and
at least one sensing unit for sensing a location parameter which depends on the position of the at least one component.

At least one embodiment of the invention further relates to a method for operating a medical device, comprising:
adjusting at least one component in a motor-driven manner, wherein the drive unit adjusting the component is actuated in accordance with a safety function so that at least one operating parameter associated with the movement of the component is restricted, wherein the safety function is requested as a function of a location parameter which depends on the position of the component.

BRIEF DESCRIPTION OF THE DRAWINGS

For a further description of the invention, reference is made to the example embodiments shown in the figures of the drawing, in which, shown schematically.

Parts which correspond to one another are provided with the same reference characters in all figures.

DETAILED DESCRIPTION OF THE EXAMPLE EMBODIMENTS

Figure 1:
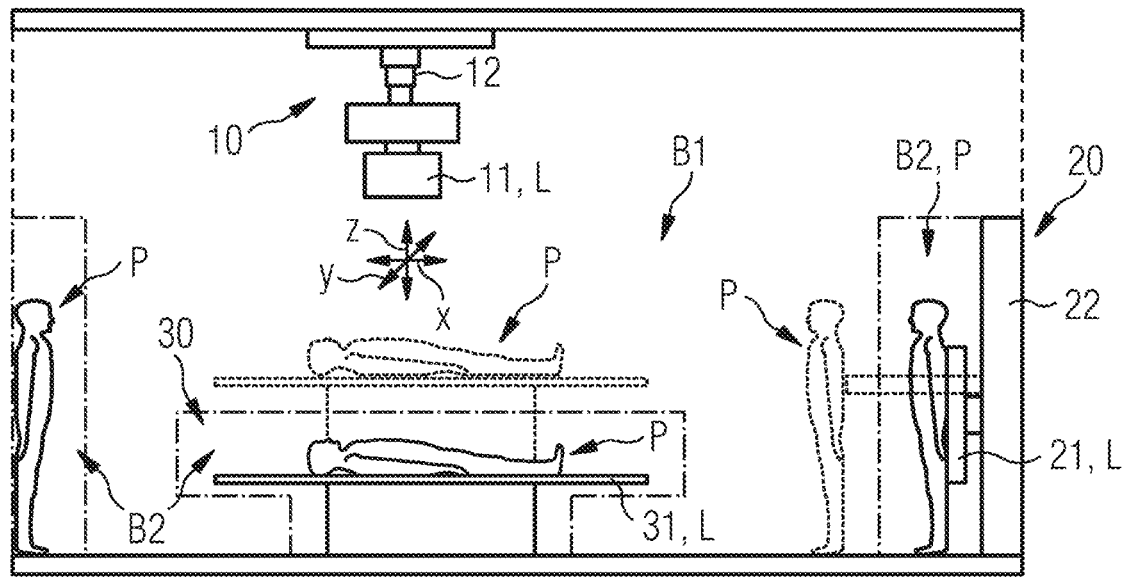
FIG. 1 shows medical devices with movably mounted components.

A medical device comprises
at least one movably mounted and motor-adjustable component,
at least one drive unit for adjusting the at least one component,
at least one motor control unit associated with the drive unit and
at least one sensing unit for sensing a location parameter which depends on the position of the at least one component.

According to an embodiment of the invention, a safety function is integrated in the motor control unit, said safety function restricting at least one operating parameter which is associated with the movement of the at least one component to be carried out, wherein a device control unit actuates the drive unit as a function of the location parameter according to the safety function.

A basic idea therefore resides in the realization of a medical device, in which the motor-driven movement of the component is executed in an intrinsically safe manner. The medical device is embodied so that there is barely any or no risk from the moving component. The medical device is embodied for instance to carry out movements with automated assistance in particular for diagnostics and/or intervention without human monitoring or completely autonomously in a further development.

On the basis of the location parameter, which characterizes the axis positions of a ceiling stand of the medical device, it is possible to decide whether the movement of the component to be carried out requires a spatial area in which people can be crushed by the moving component, i.e. relates to a spatial area from which the people are not able to withdraw unhindered or requires a spatial area in which only a temporary collision with a person can occur, i.e. a spatial area from which the person can withdraw unhindered. In other words, a classification of the spatial areas required by the movement into different danger zones takes place.

As a function of this there is provision for a restriction or limitation of the operating parameter associated with the component movement. On the apparatus side, this is implemented in that the safety function or functions restricting the operating parameter are integrated in the motor control unit. Logical relations which link the location parameter or the position and/or location of the component with permissible operating parameters, such as for instance a speed, force or a torque with which the component is moved, are implemented in the programmable apparatus control unit.

The logical link between the location parameter and operating parameter is generally too complex for an inflexible or hardwired implementation on the apparatus side. At least one embodiment of the invention advantageously faces this problem by dividing the control architecture in a manner adjusted thereto.

On account of the intrinsically safe realization of the component movement, the user of the medical device no longer has to monitor the movements independently. This enables the user to undertake other tasks provided the movement is carried out as desired. In the long term this enables the reduction in personnel costs.

Within the context of this specification the location parameter comprises or contains one or more variables, which characterize the position or the at least one movably mounted component in the room. In the development the location parameter comprises one or more variables which characterize the surroundings of the at least one movably mounted component in the room. These can be derived in particular from ambient data sensed using sensors.

In one embodiment the safety function restricts the at least one operating parameter to a maximum value, so that a speed of the component and/or a force acting on the component and/or a torque acting on the component is not exceeded. The request for the safety function ensuring the corresponding safety requirements as a function of the location parameter takes place by way of the programmable apparatus control unit.

In this context, provision is made in one embodiment to fixedly predetermine the maximum value for the at least one operating parameter. In this case, there is no adjustment to the maximum value during the controlled independent or at least semi-independent implementation of the component movement.

In one embodiment, the apparatus control unit is designed to continuously adjust the request of the safety function and the maximum value linked to the safety function as a function of the location parameter. In other words, the safety function and/or the maximum value are adjusted during the movement of the component, in other words as a function of the respective temporarily sensed value of the location parameter. In this way the apparatus control unit is embodied to predetermine variable limits or maximum values for the operating parameter, in particular for the speed and/or for the force and/or for the torque with which the component is moved.

In one embodiment, a control logic containing the request of the safety function as a function of the location parameter is implemented in a failsafe program part of the apparatus control unit. In particular, in the field of medical technology, such program parts are also referred to as first-error-proof, i.e. the failsafe program part is protected by measures known per se against an individual error (first error) resulting in an unsafe apparatus state. In other areas of industry, by contrast, a program part is in particular then referred to as failsafe if the program execution reaches a required safety standard (safety integrity level, SIL), or performance standard (performance level, PL). These standards can be specified in particular within the scope of industry standards. Accordingly control units are commercially available and are certified according to the corresponding industry standards. One example are SIMATIC failsafe controllers (e.g. S7-1500-F) by the company Siemens. Program parts which do not fulfill the required safety requirements are referred to as "functional".

In one embodiment, a communication interface between the apparatus control unit and the motor control unit is embodied to be failsafe. The apparatus control unit, the motor control unit and, as a third party, the communication interface between the apparatus control and motor control unit contribute to ensuring the intrinsic safety of the apparatus movement. For instance, a control logic is implemented in the apparatus control unit, which derives the logical link between the location parameter and a boundary parameter restricting the movement of the component. The motor control unit controls the drive unit in accordance with the at least one operating parameter so that the boundary parameter or parameters set are complied with during the movement.

The device controller can activate, deactivate or change a boundary parameter in the motor control unit by way of the communication interface, for instance. For this reason the communication interface also correspondingly fulfills the requirements of the first error safety or for instance safety requirements specified in industry standards, such as SIL or PL. The communication interface preferably has field bus topology and/or comprises at least one, for instance Ethernet-based, field bus. The communication interface is preferably embodied for the topological identification and configuration of connected electronic components. This advantageously enables the unique identification of the electronic component.

The Ethernet topology ensures that in principle only point-to-point connections are possible. A star or tree topology is only possible by using further interfaces, known as Ethernet switches, which, in turn, can establish a number of point-to-point connections to the connected subscribers or can in each case internally connect two of these terminals to one another (also: routing). Each individual communication path therefore has precisely two subscribers and the failure or recurrence of an individual subscriber can be uniquely identified by the respective other subscriber of the point-to-point connection.

In one embodiment the sensing unit comprises a near-field sensor system for identifying the component approaching an object, in particular an obstacle or a person. In this context various different sensors are considered for the near-field sensor system, such as, for instance, ultrasound sensors, which are attached to the moving component of the medical device and identify that an object is being approached.

In another example embodiment, the moveable component is in particular provided with a capacitive outer skin, which can detect that an object, in particular a person, is being approached. Alternatively or in addition, in one embodiment the near-field sensor system comprises one or more optical cameras. The near-field sensor system is actively connected to the apparatus control unit in such a way that, when the obstacle and/or the person are approached, a safety-oriented reaction is carried out automatically. For instance, the safety-oriented reaction contains a reduction in the speed and/or the force and/or the torque with which the component is moved, and/or a safety stop. Safety-oriented reactions of this type of the apparatus controller are triggered automatically depending on the situation, for instance if the distance from the person and/or obstacle reaches or does not reach a predetermined or predeterminable limit value. In the development, provision is made to trigger different reactions when the limit values associated with the respective reaction are reached or not met.

In the development, provision is made for the near-field sensor system to be provided to sense user gestures. In these example embodiments the near-field sensor system is therefore part of a user interface, which is embodied to identify and evaluate gestures.

In the embodiment, the sensing unit comprises a tactile sensor system for identifying collisions between components and objects, in particular obstacles and/or people. To this end the medical device, in particular the movably mounted component, has an outer housing, for instance, which comprises a number of spring-mounted housing sections. Upon contact from the outside, the respective housing section approaches the rigid apparatus mechanism arranged therebelow, wherein the spring is compressed. This relative movement can be detected for instance via a switch, in particular microswitch. The tactile sensor system is actively connected for instance to the apparatus control unit in such a way that in the event of contact or collision between the moving component and the obstacle or the person, a safety-oriented reaction is automatically carried out. For instance, the safety-oriented reaction, as already described above, contains a reduction in the speed and/or the force and/or the torque with which the component is moved, and/or a safety stop.

In the development, provision is made for movements of the component carried out manually by the user to be sensed. The operational force is determined in the embodiment with the aid of a force sensor. Alternatively or in addition, a sensorless sensing of the operational force takes place, i.e. without the use of a force sensor or in addition to the data provided by the force sensor. With the sensorless sensing, use is made of measuring the motor current via a correspondingly embodied sensing unit or with a correspondingly embodied current measuring device and the sensed measured value for the motor current is compared with an expected value which characterizes a known movement profile. These expected values are stored in the apparatus control unit, for instance. The operational force required to carry out the movement can be calculated in particular from the difference between measured value and expected value. In this context the apparatus control unit is therefore embodied in particular to provide a controlled force assistance for a manual movement of this type.

In one embodiment the apparatus control unit is embodied to learn control routines for movement sequences. In the apparatus control unit, an artificial intelligence is programmed in these example embodiments, which enables movement sequences carried out manually by the user to be learnt.

In one embodiment the apparatus control unit is connected to an input unit for voice control.

At least one embodiment of the invention further relates to a method for operating a medical device, including an embodiment of the medical device. Advantages associated herewith result inter alia directly from the previous description with reference to the associated appliance, so that reference is made hereto.

With at least one embodiment of the method for operating the medical device, the at least one component is motor-adjusted, wherein the drive unit adjusting the component is actuated according to at least one embodiment of the invention in accordance with the safety function so that at least one operating parameter associated with the movement of the component is restricted. The safety function is requested as a function of a location parameter, which depends on the position of the component.

In one embodiment, the at least one operating parameter is restricted to a maximum value by way of the safety function, so that a speed of the component and/or a force acting on the component and/or a torque acting on the component is not exceeded.

In one embodiment, a situation-dependent reaction is carried out automatically when the component approaches or comes into contact with an object.

In one embodiment, the situation-dependent reaction contains a reduction in the speed and/or force with which the component is moved and/or a safety stop and/or a movement in the opposite direction.

In this context, variable or fixed position limits are implemented in the embodiment. The position limits restrict in principle a position range in which a motor-driven movement of the component is permissible. The movement range of individual axis movements of movable parts is typically restricted by mechanical end stops and is thus fixedly predetermined. The movement range can therefore no longer be changed after assembling the apparatus. Conversely, in the embodiment of the invention the variable or fixed position limits are predetermined by changeable program structures. By way of the first-error safety of this position limitation ("safely limited position"), this realization is to be considered from the safety aspect as being equal to mechanical end stops. This allows for greater flexibility, in order to variably design the variable or fixed position limits as a function of the apparatus state, in particular of the current value of the location parameter, which characterizes the location or alignment of an apparatus axis of the component, for instance. As a result, e.g. the room in which the medical device is installed can be better utilized.

In one embodiment, the apparatus control unit is designed to continuously adjust the request of the safety function and the maximum value linked to the safety function as a function of the location parameter. In other words, the safety function and/or the maximum value are adjusted during the movement of the component, in other words as a function of the respective temporarily sensed value of the location parameter. In this way, the apparatus control unit is embodied to predetermine variable limits or maximum values for the operating parameter, in particular for the speed and/or for the force and/or for the torque with which the component is moved.

In one embodiment, the movement of the at least one component is triggered and/or controlled by voice signals. The voice signals are sensed for instance via one or more microphones and passed to the apparatus controller. The apparatus controller is embodied to identify the voice signals and to control the movement sequences in accordance with the voice signal, wherein the at least one operating parameter associated with the component movement is adjusted.

In one embodiment, the movement of the at least one component is triggered and/or controlled by sensed gestures of the user. The gestures are sensed for instance via the near-field sensor system. In particular, in the embodiment a camera or a number of cameras is provided for visually sensing the gestures. In these example embodiments the apparatus control unit is embodied to evaluate and identify the data sensed by the near-field sensor system so that control of the movement of the components by way of gestures is enabled.

FIG. 1 shows by way of example embodiment of a number of medical devices 10, 20, 30, which have movably mounted components 11, 21, 31. A radiography system is shown specifically in the example embodiment, which is not to be considered restrictively.

The medical device 10 is an x-ray device, which has a component 11 embodied as an x-ray emitter, which is movably mounted on a ceiling stand 12 so that this can be adjusted with respect to spatial axes X, Y, Z.

The medical device 20 is a Bucky wall stand, which has a component 21 embodied as an x-ray detector, which is movably mounted on a vertical stand 22 so that this can be adjusted at least along the spatial axis Z.

The medical device 30 is a patient couch which has a component 31 embodied as a support device for the patient and which can be adjusted at least with respect to the spatial axis Z.

Different positions which a person P, in particular a patient or a user of the respective medical device 10, 20, 30, and/or the component 11, 21, 31 can assume are likewise shown at least with dashed lines.

Different danger zones are to be defined as a function of the freedom of movement of the respective component 11, 21, and its positions or locations which are identified by location parameter L. In the region B1, there is an unblocked possibility of withdrawal for the person P. In the region B2, this possibility of withdrawal does not exist, there is therefore an increased risk of injury to the person P, which originates from the moving component 11, 21, 31.

The medical devices 10, 20, 30 are equipped with inherent safety properties, which restrict or limit the movement to be carried out with respect to at least one operating parameter BP as a function of the position or location of the respectively adjustable component 11, 21, 31. To this end, as shown schematically in FIG. 2, corresponding safety functions restricting the respective operating parameter BP are fixedly integrated in a motor control unit MSt of the respective medical device 10, 20, 30. The motor control unit MSt here controls a drive unit A, which adjusts the respective component 11, 21, 31 in a motor-driven manner.

Figure 2:
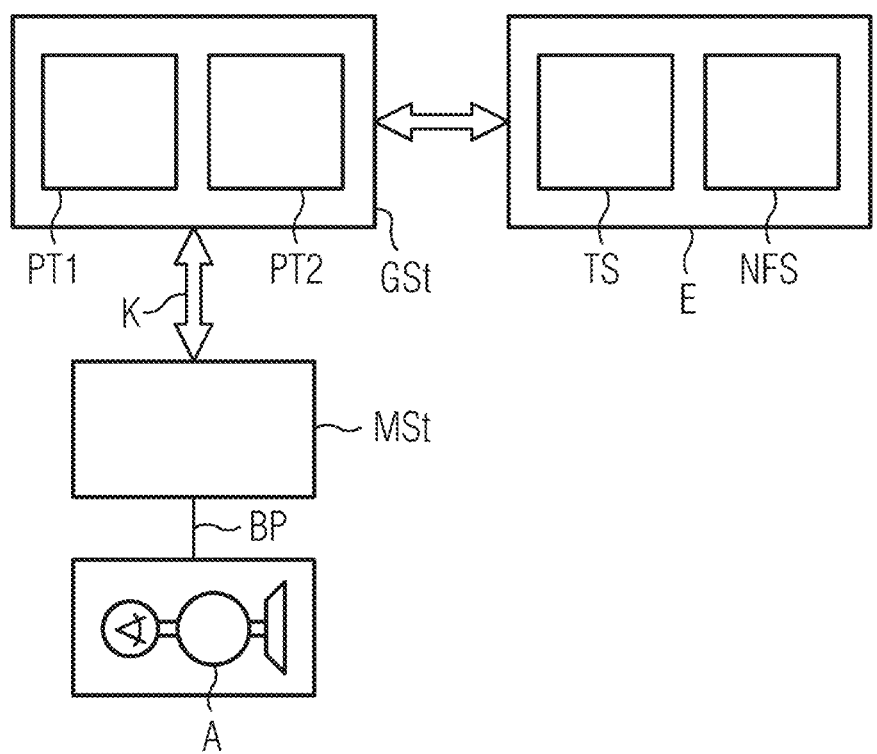
FIG. 2 shows a control architecture for the medical devices in FIG. 1 with inherent safety functions.

The control architecture is illustrated schematically in FIG. 2. A programmable apparatus control unit GSt is connected to the motor control unit MSt by way of a communication interface K with safety-oriented properties. A sensing unit E is further connected to the apparatus control unit GSt and transmits data which characterizes at least the location parameter L. As a function of the location parameter L, the apparatus control unit GSt requests the motor control unit MSt with a safety function which satisfy in particular the safety requirements associated with the regions B1 or B2. The safety function restricts the operating parameter BP, for instance a maximum speed, a maximum force and/or a maximum torque with which the component 11, 21, is moved, to a suitable maximum value. In particular, different safety functions which restrict the operating parameter BP to respectively different maximum values can be requested for the different regions B1, B2.

The apparatus controller GSt can be programmed so that the logical relations between the location parameter L characterizing the position or location of the component 11, 21, 31 can be flexibly predetermined. In one example embodiment, the programmable apparatus control unit GSt comprises a functional program part PT1 and a failsafe program part PT2, in which the safety functions are implemented.

The sensing unit E is embodied to sense the location parameter L characterizing the position or location of the component 11, 21, 31. A sensing of the surroundings of the respective medical device 10, 20, 30 is preferably also carried out. In the example embodiment shown, the sensing unit E comprises a tactile sensor system TS and a near-field sensor system NFS for identifying the component 11, 21, 31 approaching an object, in particular the person P. The tactile sensor system TS is embodied to sense mechanical shaking or forces which act on the component 11, 21, 31. This enables for instance the sensing of collisions between components 11, 21, 31 and the person P or an object.

The medical device 10, 20, 30 is embodied in the embodiment to sense a movement of the component 11, 21, 31, which is carried out manually by the user, in particular without a sensor. In this context, the apparatus control unit GSt is preferably embodied to learn a movement of the component 11, 21, 31 which is carried out manually and sensed without a sensor or with the aid of the sensing unit E, which to this end has for instance a force sensor not shown in more detail, and consequently to carry out the same in an automatically controlled manner.

Alternatively or in addition, the apparatus control unit GSt is embodied to carry out a situation-dependent reaction, such as for instance a safety stop or a movement in the opposite direction when the component 11, 21, 31 approaches, collides with or comes into mechanical contact with an object, in particular the person P. As an alternative or in addition, the apparatus control unit GSt is embodied to identify user gestures sensed via the near-field sensor system NFS and to evaluate the same. In other words, the apparatus control unit GSt is embodied for gesture control, i.e. at least one adjustment of the operating parameter BP is carried out in accordance with the sensed and evaluated gesture.

The embodiment of the medical device 10, 20, 30 which is described above with inherent safety functions enables new possibilities of triggering a movement of the component, since release switches such as dead man apparatuses or suchlike no longer have to be provided. This enables in particular a voice or gesture control of the medical device 10, 20, 30 or the component movement.

Although the invention has been illustrated and described in more detail with reference to the preferred example embodiments, the invention is not restricted hereby. Other variations and combinations can be derived from the person skilled in the art without deviating from the fundamental idea of the invention.

The invention claimed is:

1. A medical device, comprising:
   at least one movably mounted and motor-adjustable component;
   at least one drive unit to adjust the at least one movably mounted and motor-adjustable component;
   at least one motor control unit, associated with the at least one drive unit; and
   at least one sensing unit configured to sense a location parameter and to identify an object that is being approached by the at least one movably mounted and motor-adjustable component while the at least one movably mounted and motor-adjustable component is in motion, the location parameter indicating a position of the at least one movably mounted and motor-adjustable component, wherein
   a safety function is integrated in the at least one motor control unit,
   the safety function is configured to restrict at least one operating parameter associated with movement of the at least one movably mounted and motor-adjustable component, and an apparatus control unit is configured to actuate the at least one drive unit as a function of the location parameter, in accordance with the safety function and adjust a request of the safety function continuously as a function of the location parameter.

2. The medical device of claim 1, wherein the apparatus control unit includes a failsafe program including a request of the safety function as a function of the location parameter.

3. The medical device of claim 1, wherein the safety function restricts the at least one operating parameter to a maximum value so that at least one of
   a speed of the at least one movably mounted and motor-adjustable component is not exceeded,
   a force acting on the at least one movably mounted and motor-adjustable component is not exceeded, and
   a torque acting on the at least one movably mounted and motor-adjustable component is not exceeded.

4. The medical device of claim 3, wherein the apparatus control unit is configured to adjust the maximum value linked to the safety function continuously as a function of the location parameter.

5. The medical device of claim 3, wherein the apparatus control unit includes a failsafe program including a request of the safety function as a function of the location parameter.

6. The medical device of claim 3, further comprising:
   a communication interface between the apparatus control unit and the at least one motor control unit, wherein the communication interface is configured to be failsafe.

7. The medical device of claim 1, wherein the at least one sensing unit includes a tactile sensor system to identify collisions between the at least one movably mounted and motor-adjustable component the object.

8. The medical device of claim 7, wherein the object is at least one of obstacles and persons.

9. The medical device of claim 1, wherein the apparatus control unit is connected to an input unit for voice control.

10. The medical device of claim 1, further comprising a communication interface between the apparatus control unit and the at least one motor control unit, wherein the communication interface is configured to be failsafe.

11. The medical device of claim 1, wherein the at least one sensing unit includes a near-field sensor system to identify the at least one movably mounted and motor-adjustable component approaching the object.

12. The medical device of claim 1, wherein the apparatus control unit is configured to learn control routines for movement sequences.

13. The medical device of claim 11, wherein the object is at least one of an obstacle and a person.

14. A method for operating a medical device, the method comprising:
   adjusting at least one movably mounted and motor-adjustable component of the medical device, in a motor-driven manner, wherein
      a drive unit adjusting the at least one movably mounted and motor-adjustable component is actuated in accordance with a safety function to restrict at least one operating parameter associated with movement of the at least one movably mounted and motor-adjustable component,
      the safety function is requested as a function of a location parameter depending on a position of the at least one movably mounted and motor-adjustable component,
      the request of the safety function is adjusted continuously as a function of the location parameter, and
      a sensing unit is configured to identify an object that is being approached by the at least one movably mounted and motor-adjustable component while the at least one movably mounted and motor-adjustable component is in motion.

15. The method of claim 14, wherein the at least one operating parameter is restricted to a maximum value by way of the safety function so that at least one of:
   a speed of the at least one movably mounted and motor-adjustable component is not exceeded,
   a force acting on the at least one movably mounted and motor-adjustable component is not exceeded, and
   a torque acting on the at least one movably mounted and motor-adjustable component is not exceeded.

16. The method of claim 15, wherein a situation-dependent reaction is carried out when the at least one movably mounted and motor-adjustable component approaches or comes into contact with the object.

17. The method of claim 16, wherein the situation-dependent reaction contains a reduction in the at least one of
   at least one of the speed and the force with which the at least one movably mounted and motor-adjustable component is moved,
   a safety stop, and
   a movement in an opposite direction.

18. The method of claim 14, wherein the movement of the at least one movably mounted and motor-adjustable component is at least one of triggered and controlled by voice signals.

19. The method of claim 14, wherein the movement of the at least one movably mounted and motor-adjustable component is at least one of triggered and controlled by sensed gestures of a user of the medical device.

20. The method of claim 14, wherein a situation-dependent reaction is carried out when the at least one movably mounted and motor-adjustable component approaches or comes into contact with the object.

* * * * *